(12) United States Patent
Ruff

(10) Patent No.: US 10,973,906 B2
(45) Date of Patent: *Apr. 13, 2021

(54) THERAPEUTIC PEPTIDES AND VACCINES

(71) Applicant: Creative Bio-Peptides Inc., Potomac, MD (US)

(72) Inventor: Michael Ruff, Potomac, MD (US)

(73) Assignee: Creative Bio-Peptides Inc., Potomac, MD (US)

( * ) Notice: Subject to any disclaimer, the term of this patent is extended or adjusted under 35 U.S.C. 154(b) by 179 days.

This patent is subject to a terminal disclaimer.

(21) Appl. No.: 16/054,455

(22) Filed: Aug. 3, 2018

(65) Prior Publication Data
US 2019/0000964 A1 Jan. 3, 2019

Related U.S. Application Data

(60) Continuation of application No. 12/688,862, filed on Jan. 16, 2010, now Pat. No. 10,071,153, which is a division of application No. 11/426,301, filed on Jun. 23, 2006, now Pat. No. 7,700,115.

(60) Provisional application No. 60/693,088, filed on Jun. 23, 2005, provisional application No. 60/693,089, filed on Jun. 23, 2005, provisional application No. 60/693,087, filed on Jun. 23, 2005.

(51) Int. Cl.
| | |
|---|---|
| *A61K 39/21* | (2006.01) |
| *C07K 16/10* | (2006.01) |
| *A61K 39/12* | (2006.01) |
| *A61K 38/16* | (2006.01) |
| *C07K 14/005* | (2006.01) |

(52) U.S. Cl.
CPC ............ *A61K 39/21* (2013.01); *A61K 38/162* (2013.01); *A61K 39/12* (2013.01); *C07K 14/005* (2013.01); *C07K 16/1063* (2013.01); *C07K 2317/76* (2013.01); *C12N 2740/15022* (2013.01); *C12N 2740/16122* (2013.01); *C12N 2740/16134* (2013.01)

(58) Field of Classification Search
None
See application file for complete search history.

(56) References Cited

U.S. PATENT DOCUMENTS

| | | | |
|---|---|---|---|
| 5,063,206 | A | 11/1991 | Bridge et al. |
| 5,276,016 | A | 1/1994 | Pert et al. |
| 5,514,670 | A | 5/1996 | Friedman et al. |
| 5,534,495 | A | 7/1996 | Pert et al. |
| 5,739,109 | A | 4/1998 | Galpin et al. |
| 5,756,449 | A | 5/1998 | Andersen et al. |
| 5,834,429 | A | 11/1998 | Pert et al. |
| 5,863,718 | A | 1/1999 | Pert et al. |
| 6,011,014 | A | 1/2000 | Andersen et al. |
| 6,242,564 | B1 | 6/2001 | Pert et al. |
| 6,265,374 | B1 | 7/2001 | Andersen et al. |
| 7,390,788 | B2 | 6/2008 | Pert et al. |
| 7,700,115 | B2 | 4/2010 | Ruff et al. |

OTHER PUBLICATIONS

Peters et al. (Journal of Virology, Jul. 2004, p. 6915-6936).*
Kreil et al. (Annual Review Biochemistry, 1997, p. 337-345).*
Polianova et al., Chemokine receptor-5 (CCR5) is a receptor for the HIV entry inhibitor peptide T (DAPTA), Antiviral Res. 2005. 67:83-92.
Ruff et al., CD4 receptor binding peptides that block HIV infectivity cause human monocyte chemotaxis. Relationship to vasoactive intestinal polypeptide. FEBS Lett. 1987.211:17-22.
Moore et al. In vivo depression of lymphocyte traffic in sheep by VIP and HIV (AIDS)-related peptides. Immunopharmacology. 1988. 16:181-89.
Pert et al. Octapeptides deduced from the neuropeptide receptor-like pattern of antigen T4 in brain potently inhibit human immunodeficiency virus receptor binding and T-cell infectivity. Proc Natl Acad Sci U S A. 1986. 83:9254-9258.
Spisani et al. Chemotactic response of human monocytes to pentapeptide analog derived from immunodeficiency virus protein gp 120. Inflammation. 1990. 14(1):55-60.
Marastoni et al. Synthesis, metabolic stability and chemotactic activity of peptide T and its analogues. J. Peptide Protein Res. 1990.35:81-88.
Smith et al. Tritiated D-ala-peptide T binding: A pharmacologic basis for the design of drugs which inhibit HIV receptor binding. Drug Development Res. 1988. 15:371-379.
Brenneman et al. Peptide T sequences prevent neuronal cell death produced by the envelope protein (gp120) of the human immunodeficiency virus. Drug Devel Res. 1988. 15:361-369.
Rosi et al. Chemokine receptor 5 antagonist d-ALA-peptide T-amide reduces microglia and astrocyte activation within the hippocampus in a neuroinflammatory rat model of alzheimer's disease. Neuroscience. 2005. 134:671-676.
Owen et al. A theta-defensin composed exclusively of D-amino acids is active against HIV-1. J. Peptide Res.2004. 63:469-76.

(Continued)

*Primary Examiner* — Agnieszka Boesen
(74) *Attorney, Agent, or Firm* — Scott Houtteman; Houtteman Law LLC

(57) ABSTRACT

Compositions are disclosed that induce broadly HIV theraputic and vaccine inducing antibodies against diverse HIV clades and relate to the ability to identify HIV gp120-derived short peptide sequence immunogens and various therapeutic compositions made from the identified peptides which compose CCR5 binding sites. Also disclosed are methods of selecting peptide sequences that are likely candidates for drugs which will offer effective treatment in such areas as Alzheimer's disease, psoriasis, multiple sclerosis and other diseases associated with the human inflammatory cascade as well as related retroviruses such as HTLV-1, the cause of tropical spastic paraparesis.

6 Claims, 5 Drawing Sheets
Specification includes a Sequence Listing.

(56) References Cited

OTHER PUBLICATIONS

Lusso et al., Cryptic Nature of a Conserved, CD4-Inducible V3 Loop Neutralization Epitope in the Native Envelope Glycoprotein Oligomer of CCR5-Restricted, but Not CXCR4-Using, Primary Human Immunodeficiency Virus Type 1 Strains. J Virol. 2005. 79(11):6957-68.

Ruff et al., Peptide T[4-8] Is Core HIV Envelope Sequence Required for CD4 Receptor Attachment. Lancet. 1987. 330(8561):751.

Altman et al., Failure of vaccine test is setback in AIDS fight, New York Times, Sep. 22, 2007, 2 pages.

Saez-Torres et al., Peptide T does not ameliorate experimental autoimmune encephalomyelitis (EAE) in Lewis rats, Clin. Exp. Immunol. 2000. 121:151-56.

\* cited by examiner

Figures 3A-B
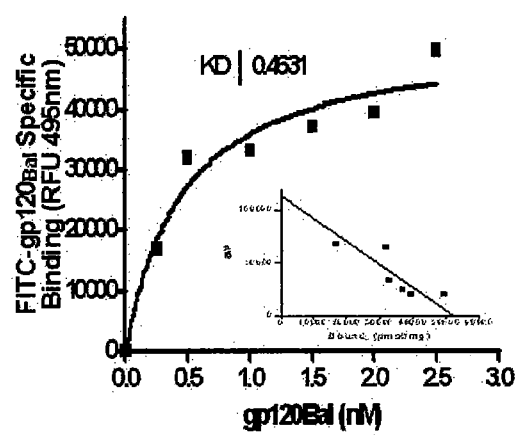
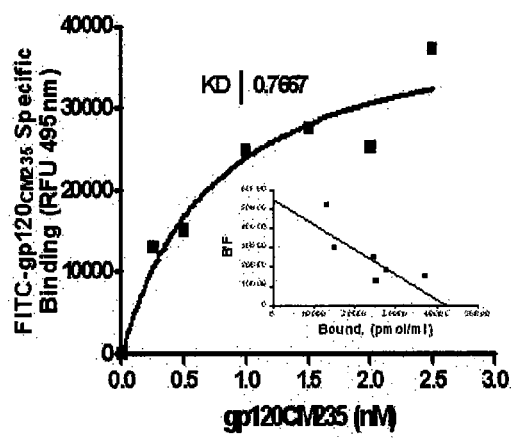

Figure 4 A-C
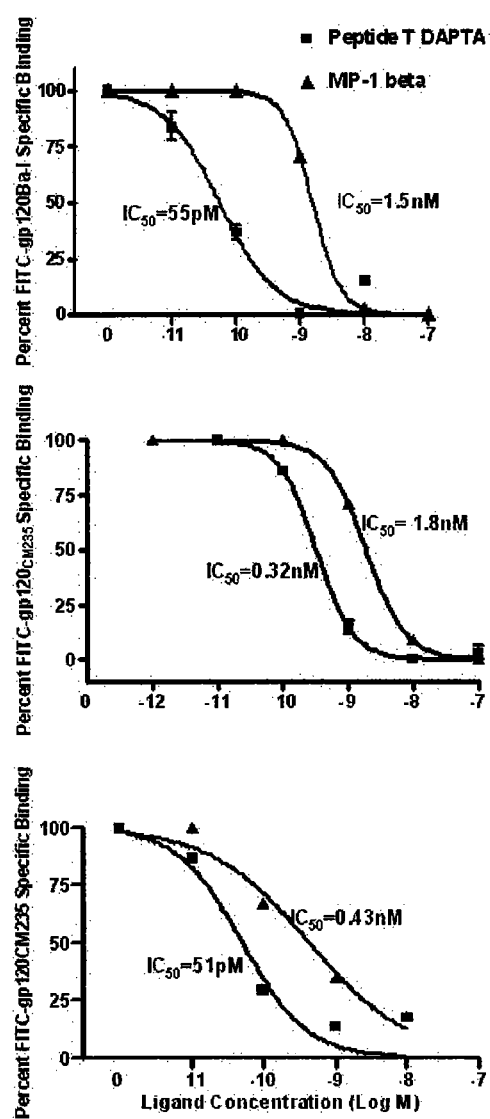

Figures 5A-B
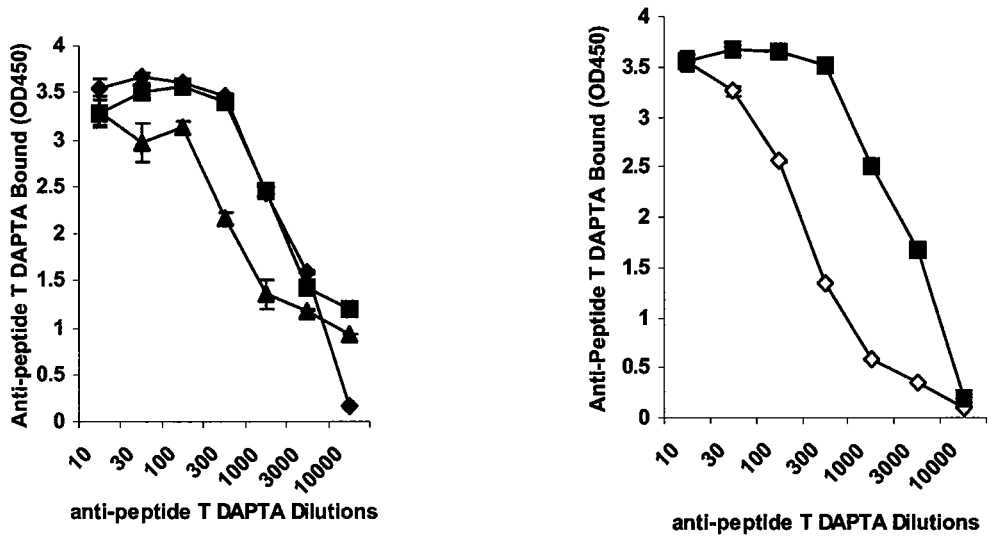
Figure 6
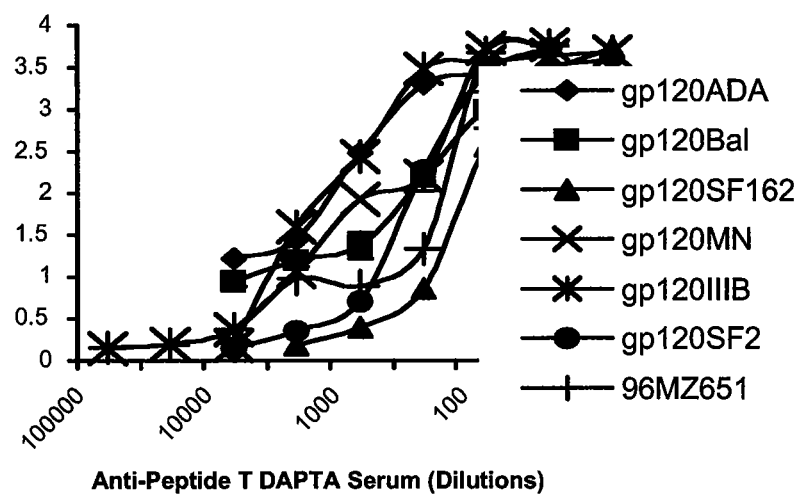

Figure 7
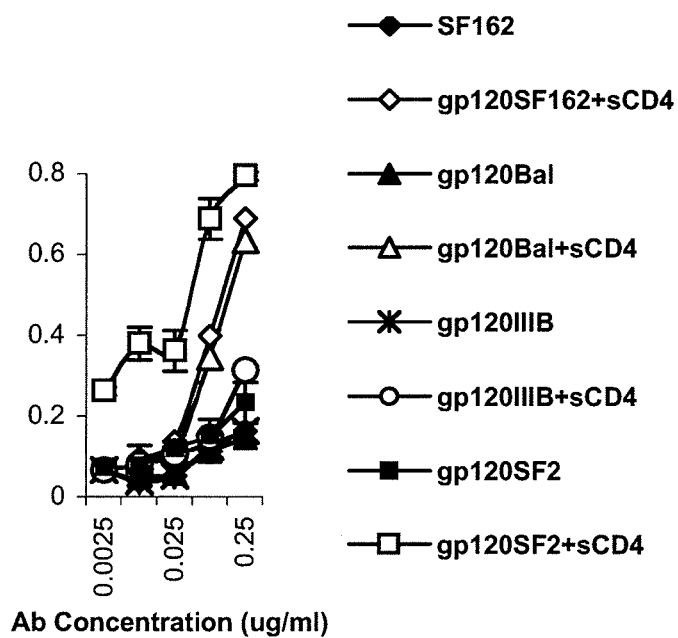
Figure 8
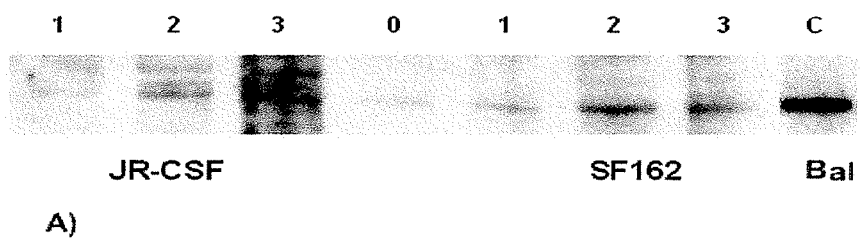

SEQUENCE LISTING

```
<160> NUMBER OF SEQ ID NOS: 91

<210> SEQ ID NO 1
<211> LENGTH: 5
<212> TYPE: PRT
<213> ORGANISM: Human immunodeficiency virus

<400> SEQUENCE: 1

Asn Thr Ser Tyr Arg
1               5

<210> SEQ ID NO 2
<211> LENGTH: 5
<212> TYPE: PRT
```

```
<213> ORGANISM: Human immunodeficiency virus

<400> SEQUENCE: 2

Ser Ser Glu Tyr Arg
1               5

<210> SEQ ID NO 3
<211> LENGTH: 5
<212> TYPE: PRT
<213> ORGANISM: Human immunodeficiency virus

<400> SEQUENCE: 3

Asn Thr Ser Tyr Met
1               5

<210> SEQ ID NO 4
<211> LENGTH: 5
<212> TYPE: PRT
<213> ORGANISM: Human immunodeficiency virus

<400> SEQUENCE: 4

Tyr Thr Ser Tyr Arg
1               5

<210> SEQ ID NO 5
<211> LENGTH: 5
<212> TYPE: PRT
<213> ORGANISM: Human immunodeficiency virus

<400> SEQUENCE: 5

Asn Thr Ser Tyr Thr
1               5

<210> SEQ ID NO 6
<211> LENGTH: 5
<212> TYPE: PRT
<213> ORGANISM: Human immunodeficiency virus

<400> SEQUENCE: 6

Asn Ser Glu Tyr Arg
1               5

<210> SEQ ID NO 7
<211> LENGTH: 5
<212> TYPE: PRT
<213> ORGANISM: Human immunodeficiency virus

<400> SEQUENCE: 7

Thr Thr Ser Tyr Arg
1               5

<210> SEQ ID NO 8
<211> LENGTH: 5
<212> TYPE: PRT
<213> ORGANISM: Human immunodeficiency virus

<400> SEQUENCE: 8

Thr Thr Ser Tyr Thr
1               5

<210> SEQ ID NO 9
<211> LENGTH: 5
<212> TYPE: PRT
<213> ORGANISM: Human immunodeficiency virus
```

```
<400> SEQUENCE: 9

Asn Thr Ser Tyr Ser
1               5

<210> SEQ ID NO 10
<211> LENGTH: 5
<212> TYPE: PRT
<213> ORGANISM: Human immunodeficiency virus

<400> SEQUENCE: 10

Ser Thr Ser Tyr Arg
1               5

<210> SEQ ID NO 11
<211> LENGTH: 5
<212> TYPE: PRT
<213> ORGANISM: Human immunodeficiency virus

<400> SEQUENCE: 11

Asn Ser Ser Tyr Arg
1               5

<210> SEQ ID NO 12
<211> LENGTH: 5
<212> TYPE: PRT
<213> ORGANISM: Human immunodeficiency virus

<400> SEQUENCE: 12

Asn Asn Ser Tyr Arg
1               5

<210> SEQ ID NO 13
<211> LENGTH: 5
<212> TYPE: PRT
<213> ORGANISM: Human immunodeficiency virus

<400> SEQUENCE: 13

Asn Thr Arg Tyr Arg
1               5

<210> SEQ ID NO 14
<211> LENGTH: 5
<212> TYPE: PRT
<213> ORGANISM: Human immunodeficiency virus

<400> SEQUENCE: 14

Ser Thr Glu Tyr Arg
1               5

<210> SEQ ID NO 15
<211> LENGTH: 5
<212> TYPE: PRT
<213> ORGANISM: Human immunodeficiency virus

<400> SEQUENCE: 15

Thr Thr Asn Tyr Thr
1               5

<210> SEQ ID NO 16
<211> LENGTH: 5
<212> TYPE: PRT
<213> ORGANISM: Human immunodeficiency virus

<400> SEQUENCE: 16
```

Asn Thr Glu Tyr Arg
1               5

<210> SEQ ID NO 17
<211> LENGTH: 5
<212> TYPE: PRT
<213> ORGANISM: Human immunodeficiency virus

<400> SEQUENCE: 17

Asn Thr Asn Tyr Arg
1               5

<210> SEQ ID NO 18
<211> LENGTH: 5
<212> TYPE: PRT
<213> ORGANISM: Human immunodeficiency virus

<400> SEQUENCE: 18

Asn Gly Ser Tyr Arg
1               5

<210> SEQ ID NO 19
<211> LENGTH: 5
<212> TYPE: PRT
<213> ORGANISM: Human immunodeficiency virus

<400> SEQUENCE: 19

Asn Ser Ser Tyr Thr
1               5

<210> SEQ ID NO 20
<211> LENGTH: 8
<212> TYPE: PRT
<213> ORGANISM: Human immunodeficiency virus

<400> SEQUENCE: 20

Ala Ser Thr Thr Thr Asn Tyr Thr
1               5

<210> SEQ ID NO 21
<211> LENGTH: 5
<212> TYPE: PRT
<213> ORGANISM: Human immunodeficiency virus

<400> SEQUENCE: 21

Thr Thr Asn Tyr Thr
1               5

<210> SEQ ID NO 22
<211> LENGTH: 5
<212> TYPE: PRT
<213> ORGANISM: Human immunodeficiency virus

<400> SEQUENCE: 22

Thr Thr Ser Tyr Thr
1               5

<210> SEQ ID NO 23
<211> LENGTH: 5
<212> TYPE: PRT
<213> ORGANISM: Human immunodeficiency virus

<400> SEQUENCE: 23

Asn Thr Ser Tyr Gly
1               5

```
<210> SEQ ID NO 24
<211> LENGTH: 5
<212> TYPE: PRT
<213> ORGANISM: Human immunodeficiency virus

<400> SEQUENCE: 24

Ser Ser Thr Tyr Arg
1               5

<210> SEQ ID NO 25
<211> LENGTH: 5
<212> TYPE: PRT
<213> ORGANISM: Human immunodeficiency virus

<400> SEQUENCE: 25

Asn Asn Arg Tyr Arg
1               5

<210> SEQ ID NO 26
<211> LENGTH: 5
<212> TYPE: PRT
<213> ORGANISM: Human immunodeficiency virus

<400> SEQUENCE: 26

Asn Thr Ser Tyr Arg
1               5

<210> SEQ ID NO 27
<211> LENGTH: 5
<212> TYPE: PRT
<213> ORGANISM: Human immunodeficiency virus

<400> SEQUENCE: 27

Ser Ser Thr Tyr Arg
1               5

<210> SEQ ID NO 28
<211> LENGTH: 5
<212> TYPE: PRT
<213> ORGANISM: Human immunodeficiency virus

<400> SEQUENCE: 28

Asn Ile Ser Tyr Thr
1               5

<210> SEQ ID NO 29
<211> LENGTH: 5
<212> TYPE: PRT
<213> ORGANISM: Human immunodeficiency virus

<400> SEQUENCE: 29

Thr Thr Asn Tyr Thr
1               5

<210> SEQ ID NO 30
<211> LENGTH: 5
<212> TYPE: PRT
<213> ORGANISM: Human immunodeficiency virus

<400> SEQUENCE: 30

Thr Ser Asn Tyr Ser
1               5
```

```
<210> SEQ ID NO 31
<211> LENGTH: 5
<212> TYPE: PRT
<213> ORGANISM: Human immunodeficiency virus

<400> SEQUENCE: 31

Asn Ser Asn Tyr Ser
1               5

<210> SEQ ID NO 32
<211> LENGTH: 5
<212> TYPE: PRT
<213> ORGANISM: Human immunodeficiency virus

<400> SEQUENCE: 32

Thr Thr Ser Tyr Arg
1               5

<210> SEQ ID NO 33
<211> LENGTH: 5
<212> TYPE: PRT
<213> ORGANISM: Human immunodeficiency virus

<400> SEQUENCE: 33

Asn Thr Ser Tyr Arg
1               5

<210> SEQ ID NO 34
<211> LENGTH: 5
<212> TYPE: PRT
<213> ORGANISM: Human immunodeficiency virus

<400> SEQUENCE: 34

Thr Ile Ser Tyr Arg
1               5

<210> SEQ ID NO 35
<211> LENGTH: 5
<212> TYPE: PRT
<213> ORGANISM: Human immunodeficiency virus

<400> SEQUENCE: 35

Thr Asp Asn Tyr Thr
1               5

<210> SEQ ID NO 36
<211> LENGTH: 5
<212> TYPE: PRT
<213> ORGANISM: Human immunodeficiency virus

<400> SEQUENCE: 36

Thr Asp Thr Tyr Thr
1               5

<210> SEQ ID NO 37
<211> LENGTH: 5
<212> TYPE: PRT
<213> ORGANISM: Human immunodeficiency virus

<400> SEQUENCE: 37

Thr Asp Ser Tyr Arg
1               5

<210> SEQ ID NO 38
<211> LENGTH: 5
```

```
<212> TYPE: PRT
<213> ORGANISM: Human immunodeficiency virus

<400> SEQUENCE: 38

Ile Asp Asn Tyr Thr
1               5

<210> SEQ ID NO 39
<211> LENGTH: 5
<212> TYPE: PRT
<213> ORGANISM: Human immunodeficiency virus

<400> SEQUENCE: 39

Ile Ser Asn Tyr Thr
1               5

<210> SEQ ID NO 40
<211> LENGTH: 5
<212> TYPE: PRT
<213> ORGANISM: Human immunodeficiency virus

<400> SEQUENCE: 40

Ile Asn Asn Tyr Thr
1               5

<210> SEQ ID NO 41
<211> LENGTH: 5
<212> TYPE: PRT
<213> ORGANISM: Human immunodeficiency virus

<400> SEQUENCE: 41

Ile Ser Asn Tyr Ser
1               5

<210> SEQ ID NO 42
<211> LENGTH: 5
<212> TYPE: PRT
<213> ORGANISM: Human immunodeficiency virus

<400> SEQUENCE: 42

Ile Glu Asn Tyr Thr
1               5

<210> SEQ ID NO 43
<211> LENGTH: 5
<212> TYPE: PRT
<213> ORGANISM: Human immunodeficiency virus

<400> SEQUENCE: 43

Val Ser Asn Tyr Thr
1               5

<210> SEQ ID NO 44
<211> LENGTH: 5
<212> TYPE: PRT
<213> ORGANISM: Human immunodeficiency virus

<400> SEQUENCE: 44

Ile Thr Asn Tyr Thr
1               5

<210> SEQ ID NO 45
<211> LENGTH: 5
<212> TYPE: PRT
<213> ORGANISM: Human immunodeficiency virus
```

<400> SEQUENCE: 45

Ile Gly Asn Tyr Thr
1               5

<210> SEQ ID NO 46
<211> LENGTH: 5
<212> TYPE: PRT
<213> ORGANISM: Human immunodeficiency virus

<400> SEQUENCE: 46

Val Asn Asn Tyr Thr
1               5

<210> SEQ ID NO 47
<211> LENGTH: 5
<212> TYPE: PRT
<213> ORGANISM: Human immunodeficiency virus

<400> SEQUENCE: 47

Ile Asp Lys Tyr Thr
1               5

<210> SEQ ID NO 48
<211> LENGTH: 5
<212> TYPE: PRT
<213> ORGANISM: Human immunodeficiency virus

<400> SEQUENCE: 48

Ile His Asn Tyr Thr
1               5

<210> SEQ ID NO 49
<211> LENGTH: 5
<212> TYPE: PRT
<213> ORGANISM: Human immunodeficiency virus

<400> SEQUENCE: 49

Ile Asp Ser Tyr Thr
1               5

<210> SEQ ID NO 50
<211> LENGTH: 5
<212> TYPE: PRT
<213> ORGANISM: Human immunodeficiency virus

<400> SEQUENCE: 50

Ile Ser Lys Tyr Thr
1               5

<210> SEQ ID NO 51
<211> LENGTH: 5
<212> TYPE: PRT
<213> ORGANISM: Human immunodeficiency virus

<400> SEQUENCE: 51

Ile Ser Thr Tyr Thr
1               5

<210> SEQ ID NO 52
<211> LENGTH: 5
<212> TYPE: PRT
<213> ORGANISM: Human immunodeficiency virus

<400> SEQUENCE: 52

Ser Ile Ile Tyr Glu
1               5

<210> SEQ ID NO 53
<211> LENGTH: 5
<212> TYPE: PRT
<213> ORGANISM: Human immunodeficiency virus

<400> SEQUENCE: 53

Ile Gly Lys Tyr Thr
1               5

<210> SEQ ID NO 54
<211> LENGTH: 5
<212> TYPE: PRT
<213> ORGANISM: Human immunodeficiency virus

<400> SEQUENCE: 54

Ile Ser Asn Tyr Lys
1               5

<210> SEQ ID NO 55
<211> LENGTH: 5
<212> TYPE: PRT
<213> ORGANISM: Human immunodeficiency virus

<400> SEQUENCE: 55

Val Ser Asn Tyr Ser
1               5

<210> SEQ ID NO 56
<211> LENGTH: 5
<212> TYPE: PRT
<213> ORGANISM: Human immunodeficiency virus

<400> SEQUENCE: 56

Ile Ala Asn Tyr Thr
1               5

<210> SEQ ID NO 57
<211> LENGTH: 5
<212> TYPE: PRT
<213> ORGANISM: Human immunodeficiency virus

<400> SEQUENCE: 57

Asn Gln Ile Tyr Glu
1               5

<210> SEQ ID NO 58
<211> LENGTH: 5
<212> TYPE: PRT
<213> ORGANISM: Human immunodeficiency virus

<400> SEQUENCE: 58

Ile Ser Gln Tyr Ser
1               5

<210> SEQ ID NO 59
<211> LENGTH: 5
<212> TYPE: PRT
<213> ORGANISM: Human immunodeficiency virus

<400> SEQUENCE: 59

Ile Asp Asp Tyr Thr

```
<210> SEQ ID NO 60
<211> LENGTH: 5
<212> TYPE: PRT
<213> ORGANISM: Human immunodeficiency virus

<400> SEQUENCE: 60

Ile Ser Ser Tyr Thr
1               5

<210> SEQ ID NO 61
<211> LENGTH: 5
<212> TYPE: PRT
<213> ORGANISM: Human immunodeficiency virus

<400> SEQUENCE: 61

Ile Ser Asp Tyr Thr
1               5

<210> SEQ ID NO 62
<211> LENGTH: 5
<212> TYPE: PRT
<213> ORGANISM: Human immunodeficiency virus

<400> SEQUENCE: 62

Val Ile Tyr Tyr Thr
1               5

<210> SEQ ID NO 63
<211> LENGTH: 5
<212> TYPE: PRT
<213> ORGANISM: Human immunodeficiency virus

<400> SEQUENCE: 63

Ile Tyr Asn Tyr Thr
1               5

<210> SEQ ID NO 64
<211> LENGTH: 5
<212> TYPE: PRT
<213> ORGANISM: Human immunodeficiency virus

<400> SEQUENCE: 64

Ile Asn Asn Tyr Ser
1               5

<210> SEQ ID NO 65
<211> LENGTH: 5
<212> TYPE: PRT
<213> ORGANISM: Human immunodeficiency virus

<400> SEQUENCE: 65

Ile Arg Gln Tyr Thr
1               5

<210> SEQ ID NO 66
<211> LENGTH: 5
<212> TYPE: PRT
<213> ORGANISM: Human immunodeficiency virus

<400> SEQUENCE: 66

Val Arg Asn Tyr Thr
1               5
```

```
<210> SEQ ID NO 67
<211> LENGTH: 5
<212> TYPE: PRT
<213> ORGANISM: Human immunodeficiency virus

<400> SEQUENCE: 67

Ile Asn Asn Tyr Ile
1               5

<210> SEQ ID NO 68
<211> LENGTH: 5
<212> TYPE: PRT
<213> ORGANISM: Human immunodeficiency virus

<400> SEQUENCE: 68

Ser Thr Ile Tyr Arg
1               5

<210> SEQ ID NO 69
<211> LENGTH: 5
<212> TYPE: PRT
<213> ORGANISM: Human immunodeficiency virus

<400> SEQUENCE: 69

Glu Tyr Ile Tyr Thr
1               5

<210> SEQ ID NO 70
<211> LENGTH: 5
<212> TYPE: PRT
<213> ORGANISM: Human immunodeficiency virus

<400> SEQUENCE: 70

Asp Thr Ile Tyr Arg
1               5

<210> SEQ ID NO 71
<211> LENGTH: 5
<212> TYPE: PRT
<213> ORGANISM: Human immunodeficiency virus

<400> SEQUENCE: 71

Ala Thr Ile Tyr Asp
1               5

<210> SEQ ID NO 72
<211> LENGTH: 5
<212> TYPE: PRT
<213> ORGANISM: Human immunodeficiency virus

<400> SEQUENCE: 72

Gly Thr Ile Tyr Gln
1               5

<210> SEQ ID NO 73
<211> LENGTH: 5
<212> TYPE: PRT
<213> ORGANISM: Human immunodeficiency virus

<400> SEQUENCE: 73

His Thr Lys Tyr Ile
1               5

<210> SEQ ID NO 74
```

```
<211> LENGTH: 5
<212> TYPE: PRT
<213> ORGANISM: Human immunodeficiency virus

<400> SEQUENCE: 74

Thr Thr Asn Tyr Thr
1               5

<210> SEQ ID NO 75
<211> LENGTH: 5
<212> TYPE: PRT
<213> ORGANISM: Human immunodeficiency virus

<400> SEQUENCE: 75

Thr Thr Asn Tyr Thr
1               5

<210> SEQ ID NO 76
<211> LENGTH: 5
<212> TYPE: PRT
<213> ORGANISM: Human immunodeficiency virus

<400> SEQUENCE: 76

Thr Thr Asn Tyr Thr
1               5

<210> SEQ ID NO 77
<211> LENGTH: 5
<212> TYPE: PRT
<213> ORGANISM: Human immunodeficiency virus

<400> SEQUENCE: 77

Asn Thr Ser Tyr Arg
1               5

<210> SEQ ID NO 78
<211> LENGTH: 5
<212> TYPE: PRT
<213> ORGANISM: Human immunodeficiency virus

<400> SEQUENCE: 78

Thr Thr Ser Tyr Thr
1               5

<210> SEQ ID NO 79
<211> LENGTH: 5
<212> TYPE: PRT
<213> ORGANISM: Human immunodeficiency virus

<400> SEQUENCE: 79

Thr Ser Asn Tyr Ser
1               5

<210> SEQ ID NO 80
<211> LENGTH: 5
<212> TYPE: PRT
<213> ORGANISM: Human immunodeficiency virus

<400> SEQUENCE: 80

Ser Ser Thr Tyr Arg
1               5

<210> SEQ ID NO 81
<211> LENGTH: 5
<212> TYPE: PRT
```

```
<213> ORGANISM: Human immunodeficiency virus

<400> SEQUENCE: 81

Asn Asn Arg Tyr Arg
1               5

<210> SEQ ID NO 82
<211> LENGTH: 5
<212> TYPE: PRT
<213> ORGANISM: Human immunodeficiency virus

<400> SEQUENCE: 82

Asn Ser Asn Tyr Ser
1               5

<210> SEQ ID NO 83
<211> LENGTH: 5
<212> TYPE: PRT
<213> ORGANISM: Human immunodeficiency virus

<400> SEQUENCE: 83

Asn Ser Ser Tyr Thr
1               5

<210> SEQ ID NO 84
<211> LENGTH: 5
<212> TYPE: PRT
<213> ORGANISM: Human immunodeficiency virus

<400> SEQUENCE: 84

Asn Ser Ser Tyr Arg
1               5

<210> SEQ ID NO 85
<211> LENGTH: 5
<212> TYPE: PRT
<213> ORGANISM: Human immunodeficiency virus

<400> SEQUENCE: 85

Asn Ser Glu Tyr Arg
1               5

<210> SEQ ID NO 86
<211> LENGTH: 5
<212> TYPE: PRT
<213> ORGANISM: Human immunodeficiency virus

<400> SEQUENCE: 86

Ser Ser Glu Tyr Arg
1               5

<210> SEQ ID NO 87
<211> LENGTH: 5
<212> TYPE: PRT
<213> ORGANISM: Human immunodeficiency virus

<400> SEQUENCE: 87

Thr Thr Ser Tyr Arg
1               5

<210> SEQ ID NO 88
<211> LENGTH: 5
<212> TYPE: PRT
<213> ORGANISM: Human immunodeficiency virus
```

-continued

```
<400> SEQUENCE: 88

Thr Ile Ser Tyr Arg
1               5

<210> SEQ ID NO 89
<211> LENGTH: 5
<212> TYPE: PRT
<213> ORGANISM: Human immunodeficiency virus

<400> SEQUENCE: 89

Tyr Ser Ser Tyr Arg
1               5

<210> SEQ ID NO 90
<211> LENGTH: 5
<212> TYPE: PRT
<213> ORGANISM: Human immunodeficiency virus

<400> SEQUENCE: 90

Ile Asn Asn Tyr Thr
1               5

<210> SEQ ID NO 91
<211> LENGTH: 5
<212> TYPE: PRT
<213> ORGANISM: Human immunodeficiency virus

<400> SEQUENCE: 91

Ile Asp Asn Tyr Thr
1               5
```

THERAPEUTIC PEPTIDES AND VACCINES

This application is a Continuation of Ser. No. 12/688,862, filed Jan. 16, 2010, now U.S. Pat. No. 10,071,153 which is a Division of Ser. No. 11/426,301, filed Jun. 23, 2006, now U.S. Pat. No. 7,700,115, and claims priority to Provisional Application Ser. No. 60/693,087, filed Jun. 23, 2005; Provisional Application Ser. No. 60/693,088, filed Jun. 23, 2005 and Provisional Application Ser. No. 60/693,089 filed Jun. 23, 2005. This application is also related to application Ser. No. 11/474,049, filed Jun. 23, 2006, now U.S. Pat. No. 7,390,788, the contents of which are incorporated herein by reference.

BACKGROUND OF THE INVENTION

It is widely believed that a vaccine capable of protecting against HIV-1 infection and AIDS will require immunogens that induce high levels of antibodies with potent neutralization activity against primary isolates of the viruses, irrespective of their geographical origin, subtype or genotype specificity a goal that current vaccine candidates fail to even approach. Therefore, identification of epitopes that mediate broad neutralization is important for rational vaccine design and development. Particularly important is the development of vaccine candidate antibodies to the Clade C sub-types, present in developing nations, compared to the predominant North American Clade B subtype, and comprising an emergent strain with world-wide relevance.

The HIV envelope is the predominant target of neutralizing antibodies in HIV-infected individuals. Some neutralization epitope clusters appear to be exposed at least partially on gp120 env protein of primary and/or monocytotropic isolates. Despite extensive studies, over 20 years, no immunogen capable of eliciting broad vaccine neutralization has been found. For this reason a vaccine against HIV infection has been elusive.

The specific invention involves identification of short sequences of gp120 which bind to the co-receptor CCR5 which identifies peptides capable eliciting antibodies with potent neutralizing activity for diverse HIV strains and peptides that are an important component of an immunization strategy for HIV-1 protection. Antibodies produced to these attachment sequences, comprising binding site peptide immunogens, are anticipated to confer protection against infection by the HIV virus, irrespective of strain, and are also expected to be therapeutic, that is their passive administration will reduce viral levels and provide clinical benefits in persons already infected with HIV The neutralizing antibody response to HIV-1 infection. Anti-human immunodeficiency virus type neutralization antibodies first appear months after the viremia following initial infection. Early-arising neutralization antibodies are highly type specific. Neutralizing antibodies response may broaden later in infection (16) but usually remain poor and occur sporadically in the majority of patients, including long-term infected individuals.

Neutralization antibodies recognize the HIV-1 envelope glycoproteins, which consist of the gp120 exterior and gp41 transmembrane glycoproteins. The gp120 glycoproteins bind the target CD4 and chemokine receptors CCR5 and CXCR4. Antibodies have in a very few instances been raised to epitopes of the gp120 which are only expressed after gp120 forms a complex with CD4. It is believed that the actual co-receptor binding site, a desired vaccine target, only forms upon CD4 association with gp120. These CD4 induced (CD4i) antibodies block CCR5 and CXCR4 binding of gp120-sCD4 complex. The number of CD4i antibodies isolated from HIV-1 infected humans is low.

Most initial work with HIV-1 vaccines was directed at developing vaccines that elicited neutralization antibodies. These neutralizing antibodies have been narrow in their action and specific almost entirely to strains of the inoculating virus in animal models. These antibodies therefore are not of broad specificity and would not make good vaccine candidates.

Most successful vaccines block virus binding to its receptor(s), which for HIV are the co-receptors CXCR4 and CC5(1, 2). Thus the identification of the co-receptor binding site, a focus of intense scrutiny for the past 20 years, which has not been accomplished until now, would be expected to produce an immunogen capable of yielding the desired broad neutralization of diverse strains suitable for vaccine use.

The subject of this application, in part, is an antibody against a biologically active co-receptor binding site. This antibody showed potent inhibition of gp120-sCD4 complex binding to the CCR5 receptor in studies in vitro and antibodies raised to the proper peptide conformation induce broadly neutralizing antibodies which are therefore expected to provide protective immunity against HIV-1 infection. i.e. a vaccine.

In over more than 10 years, only a few human MAbs that mediate broad and potent neutralization of most HIV-1 isolates have been isolated. Two of these MAbs bind to the surface of gp120 (MAbs b12 and 2G12) (3, 4), and one binds to an epitope just proximal to the membrane spanning domain of gp41. MAb b12 recognizes a complex discontinuous epitope involving the C3-V4 region of gp120 and carbohydrate. MAb 2F5 binds to a linear epitope on the ectodomain of gp41; however, the simplicity of this epitope is deceptive and probably more complex than the six-residue linear sequence MAbs b12, 2G12, and 2F5 have shown in vitro neutralizing activity against a wide variety of primary isolates. All recombinant envelope-based vaccine candidates tested so far in clinical trials, even including epitopes known to mediate broad neutralization did not elicit significant neutralizing antibodies against primary isolates. The peptide based vaccine candidates also fail to elicit adequate immune response.

Homologous sequences to peptide DAPTA (Dala1-peptide T-amide, (5)) are present within V2 of numerous HIV-1 isolates (we have examined 4,078 sequences). Our results with a polyclonal, and a purified IgG antibody against the peptide DAPTA, showed significant neutralization activity against primary and laboratory adapted strains, raising the prospect that the eight sequences from the carboxyl terminus of V2 domain, in close proximity to the bridging sheets represent a new neutralizing epitope.

Generation of Polyclonal Peptide DAPTA Antiserum.

To generate affinity purified antibodies, six rabbits were immunized by sequential subcutaneous injections of: 1) 75 μg peptide DAPTA suspended in Freund's Complete Adjuvant (day 1), 2) 75 μg DAPTA suspended in Freund's Incomplete Adjuvant (day −20) and 3) 150 μg DAPTA without adjuvant (day 35). To test for seroconversion, rabbits were bled from the ear vein on day −1 and weekly thereafter and the sera tested by enzyme-linked immunosorbent assay (ELISA) using microtiter plates coated with purified peptide DAPTA and goat anti-rabbit IgG conjugated to horseradish peroxidase. The seropositive rabbits were subsequently bled by cardiac puncture. Peptide DAPTA antibody present in the antisera was purified by affinity chromatography using affinity sepharose column coupled to purified peptide DAPTA.

BRIEF SUMMARY OF THE INVENTION

The following is a summary of some preferred embodiments and are not meant to limit the scope of the invention in any way. Compositions are disclosed that induce broadly neutralizing antibodies against diverse HIV clades, the key component of an effective vaccine.

Some embodiments relate to the ability to identify HIV gp120-derived short peptide sequence immunogens and various therapeutic compositions made from the identified peptides which compose CCR5 binding sites. The peptides are selected by analyzing peptide sequences from diverse HIV strains, sequences from related virus strains, sequences from other viral envelops and sequences from select neuropeptides.

Further, other embodiments provide for compositions that act as HIV therapeutics or when administered to humans act as immunogens to induce broadly active anti-HIV vaccine antibodies.

Still further embodiments relate to the ability to stabilize, reduce aggregation and enhance immunogenicity of peptides in therapeutically useful formulations. More specifically, the present invention provides therapeutic compositions comprising at least one self-associating, or self-aggregating, peptide or protein drug and at least one surfactant, wherein the surfactant is further comprised of at least one alkylglycoside and/or saccharide alkyl ester.

Yet still further embodiments relate to a novel method of selecting peptide sequences that are likely candidates for drugs which will offer effective treatment in such areas as Alzheimer's disease, psoriasis, multiple sclerosis and other diseases associated with the human inflammatory cascade as well as related retroviruses such as HTLV-1, the cause of tropical spastic paraparesis.

BRIEF DESCRIPTION OF THE DRAWINGS

FIGS. 3A-B. Fluorescent labeled gp120 (FITC-gp120) efficiently bound to the Cf2Th/synCCR5 cells only in presence of sCD4.

FIG. 4A-C. DAPTA inhibits gp120 envelope protein binding to CCR5.

FIGS. 5A-B. Binding of anti-peptide DAPTA to monomeric gp120.

FIG. 6. Binding Affinity of Anti-Peptide T DAPTA Serum to gp120.

FIG. 7. Soluble CD4 Dependent Binding of Anti-Peptide T DAPTA IgG to gp120 Proteins.

FIG. 8. Affinity Binding of Anti-peptide T IgG and polyclonal serum to membrane immobilized viral and recombinant gp120 proteins.

DETAILED DESCRIPTION OF THE INVENTION

Figure 1:
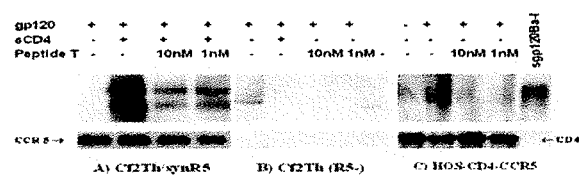
FIG. 1. DAPTA Prevents Co-Immunoprecipitation of gp120-CD4 Complex with CCR5 Receptor.

In contrast to products and methods of previous studies, the products and methods disclosed herein exhibit unexpected properties which demonstrate useful anti-HIV activity and other therapeutic properties. In the following examples, some, but not all, of the various embodiments of the invention are illustrated.

Described herein, are a family of bioactive, pentapeptides in the V2 region of gp120 with variable but homolous sequences which block co-receptor binding. In previous studies, the V2 region was thought to play no important role in gp120 binding to receptors and infectivity. It was believed that mutants lacking V2 were infectious (6, 7). In contrast to the V2 loop, the V3 loop has widely been proposed to contain the receptor binding epitopes of gp120 (7-9). Still such homologous sequences can sometimes be taught from other regions of gp160 than V2, where they can occur.

The present invention describes formulations comprising one or more peptides with receptor activity at CCR5. Homologous sequences to peptide T (derived from the SF-2 isolate) are present in similar location within V2 of numerous HIV-1 isolates. We have examined 4,078 envelope (gp120) V2 sequences available in the Entrez data bases. Of these, 60% take the form xTxYx or xNxYx, and 23% take the form xSxYx, while the remaining 17% are distributed among some 10 other minor motifs with prevalence of 2 to 7%. The importance of these diverse envelope derived pentapeptide sequences is to define receptor active motifs, such as the two major motifs which comprise over 80% of the sequences available, with some minor examples added for completeness. From this collection of structures one is able to design peptides, singularly, or in mixtures, with broad specificity against seemingly diverse HIV strains, as treatments or vaccine immunogens.

The V2 sequences we have studied occur in nearly the same location (V2, near the stem) in numerous, if not all, HIV isolates and are somewhat homologous to the terminal five amino acids of peptide T DAPTA. The peptides have homology with members of the VIP/PACAP/GHRH peptides. Many of these viral derived and neuropeptides (including those of Table 1) have been synthesized, tested and shown to possess bioactivity which is equivalent or even more potent than peptide T DAPTA octapeptide. Pharmacologically, the pentapeptides are partial antagonists of chemokine chemotaxis (10). The antagonist effect of DAPTA is due to its ability to block gp120-sCD4 binding to CCR5 (11) or block gp120-induced neuronally killing in vitro (12)

Identification of a Therapeutic and Vaccine Immunogen Library of V2 Related Pentapeptides from GP120

The following Table 1 contains a library of nineteen (19) useful pentapeptides from which therapeutic peptides and vaccine components will be selected.

TABLE 1

| SEQ ID NO. | SEQUENCE | FREQUENCY IN END OF V2 (4085 available) |
| --- | --- | --- |
| 1 | NTSYR | 1164 |
| 2 | SSEYR | 308 |
| 3 | NTSYM | 127 |
| 4 | YTSYR | 121 |
| 5 | NTSYT | 75 |
| 6 | NSEYR | 73 |

TABLE 1-continued

| SEQ ID NO. | SEQUENCE | FREQUENCY IN END OF V2 (4085 available) |
|---|---|---|
| 7 | TTSYR | 73 |
| 8 | TTSYT | 70 |
| 9 | NTSYS | 64 |
| 10 | STSYR | 63 |
| 11 | NSSYR | 50 |
| 12 | NNSYR | 41 |
| 13 | NTRYR | 38 |
| 14 | STEYR | 15 |
| 15 | TTNYT | 14 |
| 16 | NTEYR | 11 |
| 17 | NTNYR | 6 |
| 18 | NGSYR | 3 |
| 19 | NSSYT | 1 |

In the following table, V2 pentapeptides and their corresponding HIV isolates are listed.

TABLE 2

| SEQ ID NO. | | |
|---|---|---|
| 20 | SF-2 | ASTTTNYT* |
| 21 | SF-2 | TTNYT |
| 22 | IIIB | TTSYT |
| 23 | RFII | NTSYG |
| 24 | Z3 | SSTYR |
| 25 | BAL | NNRYR |
| 26 | ADA | NTSYR |
| 27 | WMJ-1 | SSTYR |
| 28 | NY5 | NISYT |
| 29 | Synthetic | TTNdY#T |

Note:
*is the sequence of peptide T, terminal pentapeptide highlighted,
is an inactive analog having a D-tyrosine in position 4 (12)
The HIV isolate for the V2 peptide is listed, then the actual peptide sequence. The peptides are recognized as analogs as the tyrosine (Y) occurs in the same position and serine (S) and threonine (T) are structurally related amino acids, differing by a single methyl group. Slight variations
are noted and these structural details have been discussed previously (18, 57). It is interesting that while peptide T is derived from the lab-adapted virus SF-2 (previously ARV, (13)) it is active against CCR5. This suggests that some of these peptides have intrinsic activity at the related CXCR4 entry receptor, and some VIP receptors (14, 15). Slight modifications would broaden receptor utilization, an effect that occurs in vivo, with the emergence of so called "dual-tropic" viral isolates late in HIV progression which also utilize the CXCR4 entry receptor.

Brain viral isolates seem to comprise a distinct envelope protein phenotype that is adapted for replication in brain microglia and macrophages which express low levels of CD4 and CCR5 (16). Envelope protein pentapeptides derived from brain viral isolates therefore may offer specific treatment advantages for blocking HIV strains, like those that infect brain, which are adapted to low CD5 or co-receptor expression. The capacity to infect cells with low CD4 and/or CCR5 would confer a broader tropism for both T cells and macrophages and therefore the pentapeptides from brain adapted strains may also be used to suppress infection of HIV strains adapted to low receptor numbers in diverse tissues and cells, not limited to brain macrophages or microglia, or to create immunogens for generation of vaccine or therapeutic antibodies. The suppression of viral isolates adapted to low receptor numbers is likely to be the next frontier in HIV therapeutics development and ligands of high potency will be most effective. By scanning for natural, virus generated sequences, biological relevance and practical utility will be optimized. Candidate therapeutic peptides can be easily tested for receptor potency and the most highly active pentapeptides brought forward as drug candidates by making additional modifications for stability and bioavailability.

V2 Receptor-Active Peptide Therapeutics and Immunogens Identified in Brain and Vaccine Pentapeptides Identified in Select Neuropeptides.

Exemplary sequences were identified from five brain isolates described in (16) and are shown in the following table

TABLE 3

| SEQ ID NO. | BRAIN V2 SEQUENCE |
|---|---|
| 30 | TSNYS |
| 31 | NSNYS |
| 32 | TTSYR |
| 33 | NTSYR |
| 34 | TISYR |

In addition to pentapeptides within V2 region of gp120, we have noted that this peptide motif exists in the other parts of gp120, in gp41 (which is membrane bound) and in neuropeptides related to VIP/PACAP/GHRH (17). Examples of these are listed in the following table.

TABLE 4

| SEQ ID NO. | NEUROPEPTIDE SEQUENCES | NEUROPEPTIDE |
|---|---|---|
| 35 | TDNYT | VIP(7-11), human, rat |
| 36 | TDTYT | VIP(7-11), chicken |
| 37 | TDSYR | GHRH (7-11), HUMAN |

Thus the V2 related peptides are demonstrated to be biologically active and the simplest explanation is that they are pharmacologically active at specific chemokine receptors.

V2 Related Pentapeptides Identified in the HIV Envelope Protein GP41

The following table illustrates GP41 HIV Sequences which may be used as therapeutics or Vaccine Immunogens.

TABLE 5

| SEQ ID NO. | SEQUENCE | FREQUENCY | PERCENTAGE (out of 702) |
|---|---|---|---|
| 38 | IDNYT | 202 | 28.8% |
| 39 | ISNYT | 192 | 27.4% |
| 40 | INNYT | 155 | 22.1% |
| 41 | ISNYS | 27 | 3.8% |
| 42 | IENYT | 19 | 2.7% |
| 43 | VSNYT | 15 | 2.1% |
| 44 | ITNYT | 9 | 1.3% |
| 45 | IGNYT | 7 | 1% |
| 46 | VNNYT | 5 | 0.7% |
| 47 | IDKYT | 5 | 0.7% |
| 48 | IHNYT | 4 | 0.6% |
| 49 | IDSYT | 4 | 0.6% |
| 50 | ISKYT | 3 | 0.4% |
| 51 | ISTYT | 3 | 0.4% |
| 52 | SIIYE | 3 | 0.4% |
| 53 | IGKYT | 2 | 0.3% |
| 54 | ISNYK | 2 | 0.3% |
| 55 | VSNYS | 2 | 0.3% |
| 56 | IANYT | 2 | 0.3% |
| 57 | NQIYE | 2 | 0.3% |
| 58 | ISQYS | 1 | 0.1% |
| 59 | IDDYT | 1 | 0.1% |
| 60 | ISSYT | 1 | 0.1% |
| 61 | ISDYT | 1 | 0.1% |
| 62 | VIYYT | 1 | 0.1% |
| 63 | IYNYT | 1 | 0.1% |
| 64 | INNYS | 1 | 0.1% |
| 65 | IRQYT | 1 | 0.1% |
| 66 | VRNYT | 1 | 0.1% |
| 67 | INNYI | 1 | 0.1% |
| 68 | STIYR | 1 | 0.1% |
| 69 | EYIYT | 1 | 0.1% |
| 70 | DTIYR | 1 | 0.1% |
| 71 | ATIYD | 1 | 0.1% |
| 72 | GTIYQ | 1 | 0.1% |
| 73 | HTKYI | 1 | 0.1% |

We examined 702 gp41 sequences from the Entrez database. All of the pentapeptide sequences recorded were located at the same position of approximately position 126 of the gp41 consistent with a shared binding function of these peptide analogs. The present invention describes formulations comprising at least one peptide or protein, whether at high or low concentration.

Identification of Diverse V2 Related Pentapeptides which Bind to CCR5 and Block HIV GP120 Binding to CCR5

Using the method described above, and in detail in (11), the binding of gp120/sCD4 complex to ChfTh-CCR5 expressing cells with or without added competitive small gp120 peptides, we show the general case that homologous peptides to the V2 derived DAPTA also have potent ability to block gp120 binding to CCR5. Structure-function activity is shown, an indicator of specificity, in that the L to D form amino acid substitution in the peptide TTNYT greatly reduced potency, and in the peptide INNYT, a N to D substitution to form the peptide IDNYT was less active. Surprisingly the all D amino acid form of the peptide TTNYT retained substantial activity indicating that all D amino acid forms of these pentapeptides are useful and may be preferred due to their expected stability to peptidase degradation.

TABLE 6

| SEQ ID NO. | Peptide | EC50 for GP120/sCD4Binding Inhibition to CCR5 (nM) |
|---|---|---|
| 74 | TTNYT | .1 nM |
| 75 | TTN(dY)T | >1000 nM |
| 76 | All D, ttnyt | 2 nM |
| 77 | NTSYR | .1 |
| 78 | TTSYT | .05 |
| 79 | TSNYS | .2 |
| 80 | SSTYR | .1 |
| 81 | NNRYR | .2 |
| 82 | NSNYS | .5 |
| 83 | NSSYT | .2 |
| 84 | NSSYR | .04 |
| 85 | NSEYR | .08 |
| 86 | SSEYR | .3 |
| 87 | TTSYR | .1 |
| 88 | TISYR | .4 |
| 89 | YSSYR | .6 |
| 90 | INNYT | .06 |
| 91 | IDNYT | 1 |

Peptide T DAPTA Prevents Gp120-SCD4 Complex Binding to CCR5 Receptors

As depicted in FIG. 1, DAPTA prevents co-immunoprecipitation of gp120-CD4 Complex with CCR5 Receptor. In the study illustrated in panel A, Cf2Th/synR5 cells expressing hCCR5 receptor were used. Solubilized CCR5 receptors were immunoprecipitated with an anti-tag antibody ID4, captured on Protein A/G agarose and incubated with gp120 Bal-sCD4 complex in presence or absence of DAPTA. Immunoprecipitated gp120 was detected by Western blotting with a human HIVIg. The same membranes were stripped and hybridized with a rabbit polyclonal antiserum against CCR5 (NT) receptor (bottom panel A). Panel B shows the cell lysates from Cf2Th parental thymocite cell line. No immunoprecipitated gp120 proteins were detected. Panel C shows HOS CD4.CCR5 cells were treated with DAPTA before incubation with gp120CM235 protein. Membrane bound CCR5 from approximately $2\times1.10^7$ were immunoprecipitated with MAb against CCR5. The coimmunoprecipitated gp120 proteins and membrane bound CD4 receptors were detected by the Western blot.

DAPTA Blocks CD4 Dependent Binding of GP120 to CCR5.

Figure 2:
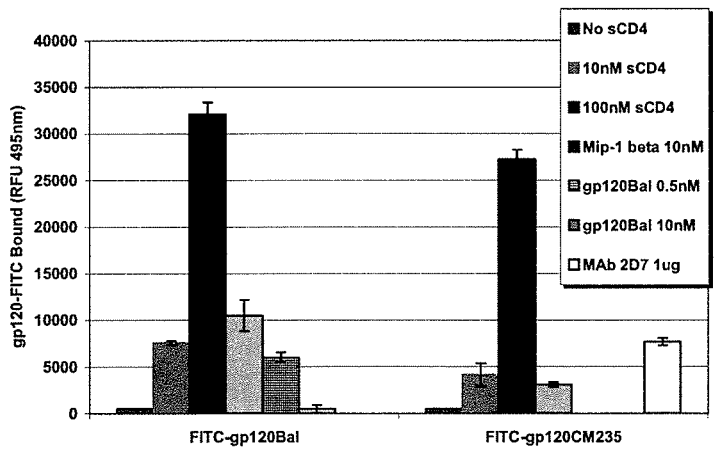
FIG. 2. CCR5 Binding Assay of GP120.

As illustrated in FIG. 2, the inventors have perfected a binding assay of gp120/sCD4 complex to CCR5 expressing cells which is sensitive to inhibition by known CCR5 ligands such as MIP1-β, or CCR5 "blocking" antibodies. The antiviral assays are described in detail in the prior art (Ruff et al., 2001, Antiviral Res, 52, 63-75), which is hereby incorporated by reference, and will be here described only briefly.

We prepared a novel FITC-labeled tracer from soluble gp120 proteins (25 µg/ml) using a Fluorescent Protein labeling kit (Roche Diagnostics GmBh). Binding assays were performed in binding buffer containing 50mM HEPES (Gibco), pH=7.4, 5 mM $MgCl_2$, 1 mM $CaCl2.6H20$ (Sigma), 5% BSA (Sigma) and 0.1% $NaN_3$, final volume 100 µl. Binding was carried out for 1 h at 37° C. in 96-well filter plates (Millipore) using several CCR5 expressing lines, as indicated. Unbound labeled proteins were removed by rapid vacuum filtration and washing using a 96-well plate manifold. Filters were counted with a fluorescent plate reader (Hewlett Packard) at 495/530 nm. Non-specific binding was determined in the absence of sCD4 and was subtracted from the gp120-FITC binding in presence of 100 nM sCD4 (total binding).

Fluorescent Labeled gp120 (FITC-gp120) Efficiently Bound to the Cf2Th/synCCR5 Cells Only in Presence of sCD4

Binding was nearly undetectable when sCD4 was not present in the assay. Maximal binding of FITC-gp120 was obtained with 100 nM sCD4, used subsequently.

As illustrated in FIG. 3, specificity of gp120 (Bal and CM235) binding was shown by competition with non-labeled HIV-1Bal, or MIP-1β, a known CCR5 ligand (18-22) (FIG. 2, above). Binding of labeled FITC-gp120Bal (0.5 nM) was inhibited by over 80% in the presence of an equimolar amount (0.5 nM), or reduced to background levels with 20-fold excess (10 nM) of non-labeled HIV-1Bal. Binding of both gp120 proteins Bal and CM235 were inhibited with the CCR5 specific ligand MIP-1β (10 nM), as previously described (23-25). Binding of FITC-gp120CM235 was also inhibited by incubation of the canine thymocyte cells with the 2D7 antibody to CCR5 (FIG. 1), which blocks gp120 binding (26). The FITC -gp120 proteins did not bind appreciably to the parental, CCR5 negative, canine thymocyte Cf2Th cells in the presence of 100 nM sCD4. These studies show CD4 dependent binding of gp120-FITC to CCR5 receptor (26-30).

Saturation binding conditions (FIG. 3) for each of two CCR5 binding gp120 proteins (Bal, CM235) were studied by adding increasing amounts (0.25 to 2.5 nM) of FITC-labeled gp120 to (Cf2Th/synR5) cell (FIG. 2, right). Non-specific binding was determined in the absence of sCD4 and was subtracted from binding, in presence of 100 nM sCD4. Saturable and high affinity binding of gp120Bal occurred with Kd of 0.46+0.17 nM (P<0.05), and with Kd of 0.77+ 0.35 nM (P<0.05) for gp120CM2351, results that are in agreement with others (27, 31, 31, 32)

DAPTA Inhibits gp120 Envelope Protein Binding to CCR5

In order to define the potency of peptide inhibitors of gp120 binding to CCR5 receptors, inhibition studies were carried out using a fixed concentration of sCD4/gp120 complex, in the presence of increasing concentrations of the CCR5 selective chemokine ligand MIP-β, and DAPTA. These studies are illustrated in FIG. 4. Total specific binding was defined as the difference in binding of FITIC-gp120 with or without added sCD4 (100 nM).

The binding of gp120BaL/sCD4 to CCR5 (Cf2Th/synR5) cells was completely inhibited by MIP-1β (IC50=1.5+0.002 nM, P<0.05) and DAPTA (IC50=55+0.08 pM, P<0.05) (FIG. 4A). The Hill slope for DAPTA was −1.07, consistent with a one-site competitive binding model. Similarly, we studied binding inhibition of gp120CMCM235/sCD4 to the same cells and again showed substantial (>80%) inhibition of specific binding by MIP-1β (IC50=1.8+0.006 nM, P<0.05) and DAPTA (IC50=0.32+0.03 nM, P<0.05) (FIG. 4B). We also show that binding of gp120CM235/sCD4 to a different, CD4-expressing, cell line (GHOST CD4.CCR5) was also inhibited by MIP-1β (IC50=0.43+0.07 nM, P<0.05) and DAPTA (IC50=51+0.09 pM, P<0.05) (FIG. 4C). Data shown (panels A-C) are the mean and sum of three experiments, each with triplicate determinations. Analyses were performed by PRISM.

The relevance of these clinical and basic research findings is that they prove the identification of the peptide T region of the gp120 as the epitope which binds to the chemokine co-receptor CCR5 (11). A nearly 25 year effort has failed to turn up clinically effective short peptide receptor competitors of CCR5. For example, two sets of all inclusive 20 mers spanning the entire gp120 molecule were prepared and tested for antiviral activity. (The second set was frameshifted 10 positions relative to the first.) None of these samples exhibited any antiviral activity. In addition, the complete failure of the 10 year, $30 Billion Federal/Private effort to identify an effective HIV vaccine, acknowledged in talks by Dr. Barney Graham, Director of Clinical Studies, at the Vaccine Research Center, NIH, would present a talk entitled, "Is an Effective HIV Possible" (Feb. 15, 2006, Bethesda, Md.), indicates the non-obviousness of our approach, which leads to the ability to create broadly neutralizing anti-HIV antibodies. It is, in fact, the inability to induce such antibodies which is the basis for the failure of all past and present vaccine attempts.

Peptides of the HIV envelope gp120 which bind to the CCR5 receptor can be used as immunogens to block virus binding to the receptor. Nearly all successful antibody vaccines work by blocking viral receptor binding or attachment.

In the last few years, analyses of the properties of formulated peptide and detailed structural studies (MacPhee, unpublished) have revealed the very strong tendency of DAPTA to aggregate upon quickly dissolving in an aqueous solution resulting in the loss of both bioavailability and antiviral activity. It is now clear that this property of DAPTA has sometimes led to suboptimal clinical results (33) and even to falsely negative in vitro results. For example, peptide T solutions have been reported to thicken and "gel," potential loss of activity and/or the ability to be transported through the mucous membrane, e.g., the nasal epithelium, was a consideration. Removing sodium chloride from the formulation and lowering the concentration to 5 mgs per ml appeared to solve the problem. However, even at only 1 mg/ml, spectropolarimetric analysis at room temperature revealed a shift from a large peak at the more dilute 0.1 mg/ml of 205.4 nm to a large peak at 237.2 nm, indicating that the Peptide T was interacting with itself at higher concentrations in aggregation steps which would lead to gelation. Electron microscopy confirmed that Peptide T formed fibrils, and to our best knowledge Peptide T forms fibrils more readily than any other small peptide yet described.

Determining Fibril Formation.

Fibril formation of peptide T or analog thereof can be determined using electron microscopy. A 2 µl aliquot of the DAPTA solution in water was applied to a formvar/carbon coated nickel EM grid. The grids were rinsed ×3 with 10 µl distilled water and stained with 10 µl of 2% uranyl acetate. The samples were examined on an FEI TEM Tecnai microscope with a LaB6 filament (120 kv) and imaged with a Megaview II CCD camera.

Fibril formation of peptide T or analog thereof can also be determined using dye binding. Congo red was dissolved in PBS (5 mM potassium phosphate, 150 mM NaCl, pH 7.4) to a concentration of 7 µg/ml. The solution was chilled to 4° C., and DAPTA added as a 10 mg/ml stock solution in water, to yield final peptide concentration in the dye solution of 0.48 mg/ml. Peptide solution immediately after dissolution of powder was compared with an aged stock solution containing aggregated peptides. Spectra were collected between 400-700 nm, at 4° C.

Fibril formation of peptide T or analog thereof can also be determined using Circular Dichroism (CD) spectroscopy. Ten mg/ml solutions in water of either freshly prepared peptide or containing fibrillar aggregates was added to distilled water at 4° C. to a concentration of 50 ug/ml. CD spectra were collected on a Jasco model J-810 spectrometer using a 0.1 cm path length quartz cuvette, between 190-250 nm, with a 1 min interval, and a response time of 2 sec.

Still another method of determining fibril formation of peptide T or analog thereof is performed using Fourier Transform Infrared (FTIR) Spectroscopy. DAPTA was dissolved in deuterated water, to a concentration of 10 mg/ml and incubated under temp and time conditions that promote fibril formation. 25 µl samples were then placed in a pre-cooled transmission cell with NaCl windows separated by a 6 um spacer. FTIR spectra were collected on a BioRad FTS-175C Fourier transform spectrometer in transmission mode using a DTGS detector. 2506 interferograms were recorded with a 2 $cm^{-1}$ resolution. Water vapor was subtracted and the spectra baselines corrected.

Immunogenic Properties

Binding of Anti-Peptide DAPTA Antibody to Monomeric Gp120

FIG. 5 illustrates the binding of anti-peptide DAPTA Antibody to monomeric gp120. In panel A, IIIB gp120 (♦); gp120 ADA (■) and gp120 Bal (▲) are directly coated on microplates (coated ELISA). Twenty five-fold serial diluted anti-peptide DAPTA was added to the wells. Bound antibody was detected by anti-rabbit IgG-HPR-donkey (KP&L) 1:1000 and measured as optical densities at 450 nm. The background was estimated by a normal rabbit serum control. Concentrations of V2 antibody required to reach half-maximal binding to all three gp120 proteins tested was between 8-25 ng/ml. The data are from a representative experiment, but each datum point is a mean value from triplicates. Panel B shows gp120 TIM reactivity with anti-peptide DAPTA in presence of sCD4 (■) and without sCD4 (◇).The antibody binds with high affinity in presence of sCD4. The results are from a representative experiment repeated twice. Each data point is mean value from triplicates.

Binding of Anti-Peptide T DAPTA Antibody to Solubilized gp120s

The affinity of anti-peptide T DAPTA antibody and the purified IgG molecule to gp120 recombinant proteins from variety of laboratory adapted viral strains were measured by the ELISA assay. Polyclonal anti-peptide T DAPTA serum bound to solubilized gp120 proteins with high affinity to gp120 ADA and gp120 IIIB and with the lowest affinity to SF162 gp120. This is illustrated in FIG. 6. The results from captured ELISA are in a good correlation with the neutralization activity and indicate that a simple ELISA test as we have here developed can discriminate vaccine candidate antibodies.

GP120s (1 µg/ml) were captured by the polyclonal goat anti-HIV-1SF gp120 serum on microplates (captured ELISA). Three-fold serially diluted anti-peptide T DAPTA serum was heat inactivated and added to the wells. Bound antibody was detected by donkey anti-rabbit IgG -HRP and measured as optical densities at 450 nm. The background was estimated by the amount of pre-immune rabbit serum against peptide T DAPTA bound and subtracted. The lines represent the data from two experiments performed in triplicates.

Binding of Anti-Peptide T DAPTA Antibody to Solubilized gp120s is CD4 Dependent

Affinity binding of purified Anti-Attachment Site IgG to gp120s with and without added soluble Cd4 (sCD4) was studied using the immunoglobulin fraction derived from the whole anti-peptide T DAPTA rabbit antiserum purified from a peptide T loaded affinity ELISA.

This is illustrated in FIG. 7. Soluble gp120 proteins were captured on microplate wells coated with anti-HIV-1SF2 serum or sCD4 (1 ug/ml). Three-fold serially diluted anti-peptide T DAPTA IgG was added in triplicate for each dilution. Bound anti-peptide T DAPTA IgG was detected by HPR-donkey anti rabbit IgG in blocking buffer with 2% normal goat serum. The results are mean of two experiments performed in triplicates. The error bars showed the SD, $p<0.05$.

Antibodies that recognize gp120 largely when bound to the CD4 molecule are of particular interest and vaccine relevance. So called CD4 induced (CD4i) antibodies inhibit CCR5 and CXCR4 binding to the gp120-CD4 complex (34-36) and so are perceived as directed against a co-receptor binding permissive conformation of gp120. The examples of CD4i antibodies isolated from humans however are limited and the prototypes exhibit only weak neutralization activity against primary HIV-1 isolates. The apparent rarity of these antibodies has been attributed to the relative inaccessibility of the CD4i epitopes (6, 37, 38).

There are only a very limited number of such antibodies that have been found to the CD4 induced (CD4i) site of gp120. An Ab that recognizes the CD4 triggered conformation of gp120 is likely to be directed against the co-receptor binding epitope. Anti-peptide T antibodies are here shown to preferentially recognize a CD4 induced epitope and are therefore presumed to bind close to or at the co-receptor binding site.

Anti-Attachment Site Abs Block Binding of GP120/sCD4 to CCR5 Entry Co-Receptor

The affinity of anti-peptide T DAPTA antiserum and the purified anti-peptide T DAPTA IgG to gp120s were studied further in Western blot. Virus particles from two HIV-1 viral strains JR-CSF and SF162 were concentrated, lysed in presence of NP40 and viral proteins were electrophoretically separated on 4-12% polyacrilamide gel. Three different concentrations were used according p24 antigen measured in the lysates—1, 2 and 3 ng per slot. Viral proteins were transferred on NEM PVDF membrane and hybridized with purified anti-peptide T DAPTA IgG (1:200). The antibody recognized the viral gp120 proteins in dose dependent manner.

This is illustrated in FIG. 8. In panel A virus particles were concentrated and separated on 4-12 SDS PAGE. The viral lysates loaded contained 1, 2 and 3 ng p24 proteins as measured by an ELISA. The membrane was hybridized with anti-peptide T DAPTA affinity purified against peptide T DAPTA IgG (1:200) and stained with HRP-donkey anti-rabbit IgG (1:2000). The film was developed with ECL solution (Amersham). The experiment was repeated twice. In panel B, whole lysate from IIIB HIV-1 viral strain and soluble gp120IIIB recombinant proteins in concentration 2 µgs/ml) were electrophoretically separated on 10% SDS PAGE and transferred. The membranes were incubated with anti-peptide T DAPTA polyclonal serum (#195), pre-bleed serum and anti-peptide T DAPTA serum in presence of peptide T DAPTA 10 µM. Specificity of anti-peptide T DAPTA antibody to HIV-1 gp120IIIB envelope proteins is shown. Peptide T DAPTA blocks anti-peptide T DAPTA binding to gp120 proteins (FIG. 8A).

Neutralization Properties of V2 Peptide-Base Antibody Anti-Peptide DAPTA.

Neutralization of HIV-1 was assessed by a syncytia count assay on HELA CD4+CXCR4/CCR5+Cells (P7). Blue focus units (BFU/well) were counted under a microscope. The data, summarized in table 7 below, were obtained using a fixed antibody concentration of 0.125 µg/well. The titrations of neutralization activity of a purified IgG were also performed. The IgG fraction followed the titration curve similar to that of polyclonal antiserum against peptide DAPTA, with lower affinity (data not shown). The inhibition of the infection is mean values of triplicates and was calculated by the formula: % Inhibition: 100−[(BFU with Ab: BFU without Ab)×100].

TABLE 7

Neutralization Activity of anti-peptide T DAPTA tested against primary and Laboratory Adapted HIV-1 Viral Strains

| Strain | Subtype | Phenotype | % Inhibition (0.125 µg/ml Abs |
|---|---|---|---|
| 92HT593 | B | X4/R5 (SI) | 33.3 |
| 92US077 | B | X4/R5 (SI) | 15.3 |
| 92US727 | B | R5 (NSI) | 0 |
| 93BR019 | B/F | R5/X4 | 96.6 |
| 93IN101 | C | R5 (NSI) | 95.9 |
| Bal | B | 5 (NSI) | 84.6 |
| JR-FL | B | R5 (NSI) | 44.7 |
| ADA | B | R5 (NSI) | 51.3 |
| IIIB | B | X4 (SI) | 35.7 |
| MN | | X4 (SI) | 69.3 |
| RF | B | X4/R5 (SI) | 11.8 |
| pNL4.3 | B | X4 (SI) | 0.9 |

To compare the potency (concentrations required to achieve 50% [$IC_{50}$] inhibition) of antibody against peptide T/DAPTA for some commonly studied clade B isolates, we used a single-round of virus infection in a focus forming assay using cell lines (HELA CD4-β galactosidase and HELA CD4.CCR5) having defined co-receptor specificity (39) (Table 7).

In the above experiments, the infection assay was performed as follows. A HeLa cell line (MAGI) was employed that both expresses high levels of CD4 and contains a single integrated copy of a beta-galactosidase gene that is under the control of a truncated human immunodeficiency virus type 1 (HIV-1) long terminal repeat (LTR) (40), and this cell line with the CCR5 gene (MAGI-CCR5) (Pirounaki et al., 2000}, were obtained from the NIAID AIDS Repository. To determine chemokine receptor subtype sensitivity of peptide T, MAGI and MAGI-CCR5, are used as described below, and were adapted from earlier protocols (40-43). Briefly, 10,000 MAGI or MAGI-CCR5 cells/well were seeded into a 96-well plate. One day later the medium was removed and dilutions of peptide T or MIP-1β were added in Opti-MEM medium (Gibco BRL, Life Technologies) with 20 µg/ml DEAE-Dextrin. The plates were cultured for 60 minutes, 37° C., 5% $CO_2$, and then dilutions of virus added with culture for a further 1.5 hrs. The viral inoculum was removed and wells washed twice with 0.2 ml Opti-MEM medium and fresh media (150 µl/well DMEM) added. After culture for a further 46 hrs. The cells were fixed for 5 min at room temperature with 1% formaldehyde, 0.2% glutaraldehyde in PBS, washed twice with PBS, stained with 4 mM potassium ferrocyanide, 4 mM potassium ferricyanide, 2 mM Mg Cl, and 0.4 mg/ml 5-bromo-4-chloro-3-indoloyl-β-D-galacto-pryanoside (X-gal stain, Inalco Pharmaceuticals, St. Luis Obispo, Calif.) in PBS at 37° C., 5% CO2, for 50 minutes, and washed twice with PBS. Blue foci were counted microscopically and infection levels were recorded as blue focus units (BFU/well). Background levels of BFU/well were typically <3 in all assays.

A crude antisera and the pre-immune control sera was tested for inhibition of infectivity of the CCR5 strains SF162 and JR-CSF in the described infection assay. Neutralization titers ($IC_{50}$) ranged from 1:20 to 1:40 dilution in the immune sera and non-specific neutralization in the pre-immune sera was negligible (not shown).

In order to enhance the specificity and potency an affinity purified antisera was prepared for further studies using a peptide T/DAPTA column. Neutralization titers of the affinity purified antibody fraction for the CCR5 strains SF162 and JR-CSF was between 0.25-125 µg/ml for SF162 and 0.125 and 0.06 µg/ml for JR-CSF viral strain (not shown). The titration of neutralization activity of the purified IgG fraction followed the titration curve similar to that of the polyclonal serum against the gp120 co-receptor attachment site with lower affinity for SF162 vaccine strain. Pre-bleed sera were tested in the same analyses. The background inhibition ranged between 2-4 percent at 1:20 diluted serum samples. The activity of the gp120 co-receptor attachment site affinity-purified Ig was next evaluated in a larger sample of HIV isolates chosen for their diversity and representation from among different clades.

A cut off value of 19% is based on the 95% confidence level obtained with normal rabbit serum (Laboratory of Antiviral Drug Mechanisms, Science Applications International Corporation at Frederick National Cancer Institute-Frederick Cancer Research and Development Center), tested at 1:5 dilutions. The results are from at least two independent experiments for each viral strain performed in triplicates.

The gp120 co-receptor attachment site affinity purified immunoglobulin showed very high neutralization activity against two primary isolates, 93BR019 from clade B/F and 93IN101 clade C viral strains and significant neutralizing activity against all but two strains. The activity against X4 viral isolates was unexpected and indicates that these peptides may be useful to create immunogens or therapeutics against R5, X4, and dual-tropic HIV strains.

Neutralization of HIV by an Affinity Pure Anti-Peptide T

Neutralization activity of anti-attachement site IgG with IC50 0.045 µg/ml against HIV-1 clade C isolates (Du123 and Du156) has been confirmed in a single round luciferase reporter gene assay by the Duke University AIDS Vaccine Lab. (David Montefiori, personal communication). The data are as follows:

TABLE 8

| Virus | SF162.LS | SS1196.1 | 6101.10 | 6535.3 | Du123.6 | Du156.12 |
|---|---|---|---|---|---|---|
| Clade | B | B | B | B | C | C |
| (Affinity pure Ig) | >0.125 µg/ml | 0.08 µg/ml | 0.05 µg/ml | 0.06 µg/ml | 0.04 µg/ml | 0.05 µg/ml |

Values are the serum dilution at which relative luminescence units (RLU) were reduced 50% compared to virus control wells (no test sample) in TZM-bl cells. Samples with activity are in bold.

Repeated Sequences

Useful pentapeptide sequences, can also be identified by their repetitive motif, occurring 2 to 5 times in a linear array either unseparated or separated by anywhere from 1 to several hundred amino acids, ie not occurring in V2 but in any other part of the envelop protein. The undesirable aggregation property of these peptides may be useful for constructing the viral envelop tertiary structure with these pentapeptide sequences serving as sites of "staple-like" adherence within the envelop. In any case, repetition of pentapeptide sequences within any given virus can teach additional useful sequences even if they do not conform to rules. For example, the repeat EYIYT was repeated five times. This repeat does not closely follow a consensus sequence. Never-the-less because it repeats, it is added to the library of active compounds.

CCR5 Receptor Activity Present

Useful candidates will have preserved affinity for the CCR5 receptor. Accordingly, assaying activity (binding assays, antiviral or other CCR5 receptor assays of relative bioactivity) of various pentapeptide compositions (i.e. with their various linkers and immunogens attached) for relative affinity to CCR5 receptors will be an additional useful screen. The higher the affinity for CCR5 receptors the greater the likelihood that the end product will have therapeutic activity.

Useful candidates will typically exhibit broad antiviral activity prior to being used as immunogens. Thus, these vaccines by themselves are expected to be therapeutic.

An especially important aspect of the invention relates to the pharmacological action of these peptides as mixed-agonists. The mixed (partial) agonist version of a drug is a clinically favored type of receptor interaction as noted by Nobelist Arvid Carlsson (Medicine/Physiology, 2000). Desensitization, resistance, and side effects of the full antagonist are typically avoided for mixed/partial agonist drugs and pharmaceutical companies have created successful drugs of this type. Partial agonist drugs work to balance receptor activity (See Redwine, 1999, which shows the mixed-agonist aspects of DAPTA action) and therefore are preferred therapeutics. We developed the methods here described to determine the intrinsic biological activity of these peptides and sought the creation of mixed-agonists such as the peptides of Table 6, which as expected, has not shown to induce resistance at the receptor after 6 months human administration.

HIV-1 gp120 is one of the most extensively glycosylated proteins. It contains 23 or 24 N-linked glycosylation sites, and the glycans attached to these sites account for approximately one-half of the protein's total mass. Numerous studies using glycosylation and glycosidase inhibitors have revealed the importance of the carbohydrate moieties in determining the conformation of the HIV-1 envelope glycoprotein. Site-directed mutagenesis indicated that most of the glycosylation sites were individually dispensable. Of the 24 sites, only 5 (amino acids 88, 141, 197, 262, and 276), all of which are located in the amino-terminal half of gp120, affected virus infectivity. The site 197 occurs in the V2 near or at the location of most of the binding site peptides we have defined. For example, note that the glycosylation motif T/SxN is often present in the peptides of the invention. Our results indicate that an N-linked glycosylation site is often near, at, or within the pepides of the specification and further defines the virus binding epitope to co-receptors like CCR5. The glycosylation, if present, may contribute to structural specificity or mask neutralization by natural antibodies as a means to avoid immune surveillance of this critical epitope.

One embodiment of the invention is a composition with immunogenic properties. This composition is described, in general as a combination of A-L-P-C moieties wherein A is any adjuvant, L is any linking moiety, P is a peptide moiety and C is a protecting group.

In the disclosed compounds, any adjuvant can be used. The peptide and linker regions are thought to act independently of the adjuvant and thus do not limit the choice of adjuvant in any way. Some, but not all examples of useful adjuvant are: any human acceptible adjuvant, hepititus core antigen, polylysine, etc. It is belevied that even adjuvant developed after this disclosure will work as well as those developed before.

Alternatively, an adjuvant can be dispensed with under certain circumstances. For example, if the peptides are made to aggregate.

Another embodiment of the invention is a composition with therapeutic properties. This composition is described, in general as a combination of L-P-C moieties wherein L is any moiety, but preferable a short peptide moiety, P is another peptide moiety and C is a protecting group.

With regard to the length of the combined L and P regions, it is believed that every specific length from about 7 to about 16 aminos acids will function. In a prefered embodiment the combined range is 7 to 11. In a still further prefered embodiment the combined range is 7 to 9. Yet another preferred embodiment is 8. Alternatively, since natural neural peptides exist that are 28 amino acids, it is believed that the peptide regions of the disclosed compositions can be about 28 amino acids in length. (See Table 4).

The various compounds disclosed herein are designed to work alone or in combination, as cocktails. Any number of different compounds can be used with no upper limit. It is believed that most useful cocktails will consist of from 2 to 7 different compounds.

The C moiety can be any protecting group. A preferred embodiment is amide.

The disclosure also encompasses compounds and methods of screening for compounds having the following activities: suppression of HIV in R5 or dual-tropic (R5/X4) strains, in monocyte-derived macrophages (MDMs), microglia, or T cells in persons infected with the HIV virus. Other activities include any human diseases treatable by modulation of CCR5 receptors including but not limited to Neuroinflammation causing Alzheimers, Multiple scxlerosis, psoriasis and arthritis. These shall be suppressed or eliminated and disease processes stopped or reversed, and clinical benefits will occur.

Finally, the disclosure encompasses methods of screening for the stability of the composition. This is determined by a biological characterization method selected from the group consisting of viral infectivity, chemotaxis, MAP Kinase activation, gp120 binding, CCR5 activation or inhibition, or G-protein signalling.

LITERATURE CITED

1. Berger, E. A., P. M. Murphy, and J. M. Farber. 1999. Chemokine receptors as HIV-1 coreceptors: roles in viral entry, tropism, and disease. *Annu Rev Immunol.* 17: 657-700.
2. Raport, C. J., J. Gosling, V. L. Schweickart, P. W. Gray, and I. F. Charo. 1996. Molecular cloning and functional characterization of a novel human CC chemokine receptor (CCR5) for RANTES, MIP-1beta, and MIP-1alpha. *J Biol Chem.* 271: 17161-17166.
3. Zwick, M. B., R. Kelleher, R. Jensen, A. F. Labrijn, M. Wang, G. V. J. Quinnan, P. W. Parren, and D. R. Burton. 2003. A novel human antibody against human immunodeficiency virus type 1 gp120 is V1, V2, and V3 loop dependent and helps delimit the epitope of the broadly neutralizing antibody immunoglobulin G1 b12. *J Virol.* 77: 6965-6978.
4. Armbruster, C., G. M. Stiegler, B. A. Vcelar, W. Jager, U. Koller, R. Jilch, C. G. Ammann, M. Pruenster, H. Stoiber, and H. W. Katinger. 2004. Passive immunization with the anti-HIV-1 human monoclonal antibody (hMAb) 4E10 and the hMAb combination 4E10/2F5/2G12. *J Antimicrob Chemother.* 54: 915-920.
5. Pert, C. B., J. M. Hill, M. R. Ruff, R. M. Berman, W. G. Robey, L. O. Arthur, F. W. Ruscetti, and W. L. Farrar. 1986. Octapeptides deduced from the neuropeptide receptor-like pattern of antigen T4 in brain potently inhibit human immunodeficiency virus receptor binding and T-cell infectivity. *Proc Natl Acad Sci USA.* 83: 9254-9258.
6. Cao, J., N. Sullivan, E. Desjardin, C. Parolin, J. Robinson, R. Wyatt, and J. Sodroski. 1997. Replication and neutralization of human immunodeficiency virus type 1 lacking the V1 and V2 variable loops of the gp120 envelope glycoprotein. *J. Virol.* 71: 9808-9812.
7. Kwong, P. D., R. Wyatt, J. Robinson, R. W. Sweet, J. Sodroski, and W. A. Hendrickson. 1998. Structure of an HIV gp120 envelope glycoprotein in complex with the CD4 receptor and a neutralizing human antibody. *Nature.* 393: 648-659.
8. Ebenbichler, C., P. Westervelt, A. Carrillo, T. Henkel, D. Johnson, and L. Ratner. 1993. Structure-function relationships of the HIV-1 envelope V3 loop tropism determinant: evidence for two distinct conformations. *AIDS.* 7:639-646.
9. Ling, H., O. Usami, P. Xiao, H. X. Gu, and T. Hattori. 2004. The N-terminal of the V3 loop in HIV type 1 gp120 is responsible for its conformation-dependent interaction with cell surface molecules. *AIDS Res Hum Retroviruses.* 20: 213-218.
10. Redwine, L. S., C. B. Pert, J. D. Rone, R. Nixon, M. Vance, B. Sandler, M. D. Lumpkin, D. J. Dieter, and M. R. Ruff 1999. Peptide T blocks GP120/CCR5 chemokine receptor-mediated chemotaxis. *Clin Immunol.* 93: 124-131.
11. Polianova, M. T., F. W. Ruscetti, C. B. Pert, and M. R. Ruff 2005. Chemokine receptor-5 (CCR5) is a receptor for the HIV entry inhibitor peptide T (DAPTA). *Antiviral Res.* 67: 83-92.
12. Brenneman, D. E., J. M. Buzy, M. R. Ruff, and C. B. Pert. 1988. Peptide T sequences prevent neuronal cell death produced by the envelope protein (gp120) of the human immunodeficiency virus. *Drug Devel Res.* 15:361-369.
13. Sanchez-Pescador, R., M. D. Power, P. J. Barr, K. S. Steimer, M. M. Stempien, S. L. Brown-Shimer, W. W. Gee, A. Renard, A. Randolph, J. A. Levy, and e. al. 1985. Nucleotide sequence and expression of an AIDS-associated retrovirus (ARV-2). *Science.* 227: 484-492.
14. Sacerdote, P., M. R. Ruff, and C. B. Pert. 1987. Vasoactive intestinal peptide 1-12: a ligand for the CD4 (T4)/human immunodeficiency virus receptor. *J Neurosci Res.* 18: 102-107.
15. Ruff, M. R., B. M. Martin, E. I. Ginns, W. L. Farrar, and C. B. Pert. 1987. CD4 receptor binding peptides that block HIV infectivity cause human monocyte chemotaxis. Relationship to vasoactive intestinal polypeptide. *FEBS Lett.* 211: 17-22.
16. Peters, P. J., J. Bhattacharya, S. Hibbitts, M. T. Dittmar, G. Simmons, J. Bell, P. Simmonds, and P. R. Clapham. 2004. Biological analysis of human immunodeficiency virus type 1 R5 envelopes amplified from brain and lymph node tissues of AIDS patients with neuropathology reveals two distinct tropism phenotypes and identifies envelopes in the brain that confer an enhanced tropism and fusigenicity for macrophages. *J Virol.* 78: 6915-6926.
17. Mulroney, S. E., K. J. McDonnell, C. B. Pert, M. R. Ruff, Z. Resch, W. K. Samson, and M. D. Lumpkin. 1998. HIV gp120 inhibits the somatotropic axis: a possible GH-releasing hormone receptor mechanism for the pathogenesis of AIDS wasting. *Proc Natl Acad Sci USA.* 95: 1927-1932.
18. Alkhatib, G., C. Combadiere, C. C. Broder, Y. Feng, P. E. Kennedy, P. M. Murphy, and E. A. Berger. 1996. CC CKR5: a RANTES, MIP-1alpha, MIP-1beta receptor as a fusion cofactor for macrophage-tropic HIV-1. *Science.* 272: 1955-1958.
19. Choe, H., M. Farzan, Y. Sun, N. Sullivan, B. Rollins, P. D. Ponath, L. Wu, C. R. Mackay, G. LaRosa, W. Newman, N. Gerard, C. Gerard, and J. Sodroski. 1996. The beta-chemokine receptors CCR3 and CCR5 facilitate infection by primary HIV-1 isolates. *Cell.* 85: 1135-1148.
20. Deng, H., R. Liu, W. Ellmeier, S. Choe, D. Unutmaz, M. Burkhart, P. Di Marzio, S. Marmon, R. E. Sutton, C. M. Hill, C. B. Davis, S. C. Peiper, T. J. Schall, D. R. Littman, and N. R. Landau. 1996. Identification of a major co-receptor for primary isolates of HIV-1. *Nature.* 381: 661-666.
21. Doranz, B. J., J. Rucker, Y. Yi, R. J. Smyth, M. Samson, S. C. Peiper, M. Parmentier, R. G. Collman, and R. W. Doms. 1996. A dual-tropic primary HIV-1 isolate that uses fusin and the beta-chemokine receptors CKR-5, CKR-3, and CKR-2b as fusion cofactors. *Cell.* 85: 1149-1158.
22. Dragic, T., V. Litwin, G. P. Allaway, S. R. Martin, Y. Huang, K. A. Nagashima, C. Cayanan, P. J. Maddon, R. A. Koup, J. P. Moore, and W. A. Paxton. 1996. HIV-1 entry into CD4+ cells is mediated by the chemokine receptor CC-CKR-5 [see comments]. *Nature.* 381: 667-673.
23. Samson, M., O. Labbe, C. Mollereau, G. Vassart, and M. Parmentier. 1996. Molecular cloning and functional expression of a new human CC-chemokine receptor gene. *Biochemistry.* 35: 3362-3367.

24. Combadiere, C., S. K. Ahuja, H. L. Tiffany, and P. M. Murphy. 1996. Cloning and functional expression of CC CKR5, a human monocyte CC chemokine receptor selective for MIP-1(alpha), MIP-1(beta), and RANTES. *J Leukoc Biol.* 60: 147-152.
25. Raport, C. J., J. Gosling, V .L. Schweichart, P. Gray, and I. F. Charos. 1996. Molecular cloning and functional characterization of a novel human CC chemokine receptor (CCR%) for RANTES, MIP-1☐, and MIP-1 ☐☐☐*J. Biolog. Chem.* 271: 17161-17166.
26. Wu, L., W. A. Paxton, N. Kassam, N. Ruffing, J. B. Rottman, N. Sullivan, H. Choe, J. Sodroski, W. Newman, R. A. Koup, and C. R. Mackay. 1997. CCR5 levels and expression pattern correlate with infectability by macrophage-tropic HIV-1, in vitro. *J Exp Med.* 185: 1681-1691.
27. Doranz, B. J., S. S. Baik, and R. W. Doms. 1999. Use of a gp120 binding assay to dissect the requirements and kinetics of human immunodeficiency virus fusion events. *J Virol.* 73: 10346-10358.
28. Martin, K. A., R. Wyatt, M. Farzan, H. Choe, L. Marcon, E. Desjardins, J. Robinson, J. Sodroski, C. Gerard, and N. P. Gerard. 1997. CD4-independent binding of SIV gp120 to rhesus CCR5. *Science.* 278: 1470-1473.
29. Trkola, A., J. Matthews, C. Gordon, T. Ketas, and J. P. Moore. 1999. A cell line-based neutralization assay for primary human immunodeficiency virus type 1 isolates that use either the CCR5 or the CXCR4 coreceptor. *J Virol.* 73: 8966-8974.
30. Moore, J. P., and J. Sodroski. 1996. Antibody cross-competition analysis of the human immunodeficiency virus type 1 gp120 exterior envelope glycoprotein. *J Virol.* 70: 1863-1872.
31. Doms, R. W. 2000. Beyond receptor expression: the influence of receptor conformation, density, and affinity in HIV-1 infection. *Virology.* 276: 229-237.
32. Mondor, I., M. Moulard, S. Ugolini, P. J. Klasse, J. Hoxie, A. Amara, T. Delaunay, R. Wyatt, J. Sodroski, and Q. J. Sattentau. 1998. Interactions among HIV gp120, CD4, and CXCR4: dependence on CD4 expression level, gp120 viral origin, conservation of the gp120 COOH— and NH2-termini and V1/V2 and V3 loops, and sensitivity to neutralizing antibodies. *Virology.* 248: 394-405.
33. Simpson, D. M., D. Dorfman, R. K. Olney, G. McKinley, J. Dobkin, Y. So, J. Berger, M. B. Ferdon, and B. Friedman. 1996. Peptide T in the treatment of painful distal neuropathy associated with AIDS: results of a placebo-controlled trial. The Peptide T Neuropathy Study Group. *Neurology.* 47: 1254-1259.
34. Babcock, G. J., T. Mirzabekov, W. Wojtowicz, and J. Sodroski. 2001. Ligand binding characteristics of CXCR4 incorporated into paramagnetic proteoliposomes. *J Biol Chem.* 276: 38433-38440.
35. Trkola, A., T. Dragic, J. Arthos, J. M. Binley, W. C. Olson, G. P. Allaway, C. Cheng-Mayer, J. Robinson, P. J. Maddon, and J. P. Moore. 1996. CD4 dependent, antibody-sensitive interactions between HIV-1 and its co-receptor CCR5. *Nature.* 384: 184-187.
36. Wu, L., N. P. Gerard, R. Wyatt, H. Choe, C. Parolin, N. Ruffing, A. Borsetti, A. A. Cardoso, E. Desjardin, W. Newman, C. Gerard, and J. Sodroski. 1996. CD4-induced interaction of primary HIV-1 gp120 glycoproteins with the chemokine receptor CCR-5. *Nature.* 384: 179-183.
37. Sullivan, N., Y. Sun, Q. Sattentau, M. Thali, D. Wu, G. Denisova, J. Gershoni, J. Robinson, J. Moore, and J. Sodroski. 1998. CD4-Induced conformational changes in the human immunodeficiency virus type 1 gp120 glycoprotein: consequences for virus entry and neutralization. *J Virol.* 72: 4694-4703.
38. Kwong, P. D., M. L. Doyle, D. J. Casper, C. Cicala, S. A. Leavitt, S. Majeed, T. D. Steenbeke, M. Venturi, I. Chaiken, M. Fung, H. Katinger, P. W. Parren, J. Robinson, R. D. Van, L. Wang, D. R. Burton, E. Freire, R. Wyatt, J. Sodroski, W. A. Hendrickson, and J. Arthos. 2002. HIV-1 evades antibody-mediated neutralization through conformational masking of receptor-binding sites. *Nature.* 420: 678-682.
39. Ruff, M. R., L. M. Melendez-Guerrero, Q. E. Yang, W. Z. Ho, J. W. Mikovits, C. B. Pert, and F. A. Ruscetti. 2001. Peptide T inhibits HIV-1 infection mediated by the chemokine receptor-5 (CCR5). *Antiviral Res.* 52: 63-75.
40. Kimpton, J., and M. Emerman. 1992. Detection of replication-competent and pseudotyped human immunodeficiency virus with a sensitive cell line on the basis of activation of an integrated beta-galactosidase gene. *J Virol.* 66: 2232-2239.
41. Harrington, R. D., and A. P. Geballe. 1993. Cofactor requirement for human immunodeficiency virus type 1 entry into a CD4-expressing human cell line. *J Virol.* 67: 5939-5947.
42. Vodicka, M. A., W. C. Goh, L. I. Wu, M. E. Rogel, S. R. Bartz, V. L. Schweickart, C. J. Raport, and M. Emerman. 1997. Indicator cell lines for detection of primary strains of human and simian immunodeficiency viruses. *Virology.* 233: 193-198.
43. Pirounaki, M., N. A. Heyden, M. Arens, and L. Ratner. 2000. Rapid phenotypic drug susceptibility assay for HIV-1 with a CCR5 expressing indicator cell line. *J Virol Methods.* 85: 151-161.

What is claimed is:

1. A therapeutic peptide derived from an HIV envelope protein, with pharmacologic activity as a result of membrane receptor binding activity, having an amino acid sequence comprising:

a contiguous sequence of 5 amino acids having the sequence selected from the group consisting of:

```
                              (SEQ ID NO: 15)
Thr Thr Asn Tyr Thr, (SEQ ID NO: 24)
Ser Ser Thr Tyr Arg, (SEQ ID NO: 8)
Thr Thr Ser Tyr Thr, (SEQ ID NO: 23)
Asn Thr Ser Tyr Gly, (SEQ ID NO: 1)
Asn Thr Ser Tyr Arg (SEQ ID NO: 40)
Ile Asn Asn Tyr Thr,
```

-continued

```
                              (SEQ ID NO: 38)
Ile Asp Asn Tyr Thr (SEQ ID NO: 35)
Thr Asp Asn Tyr Thr,
and (SEQ ID NO: 13)
Asn Thr Arg Tyr Arg;
``` wherein each of the five amino acids of the SEQ ID is a D stereo isomer, and wherein the peptide has an overall length of five to nine amino acids.

2. The therapeutic peptide of claim 1 wherein said peptide overall length is five amino acids.

3. The therapeutic peptide of claim 1 wherein said peptide overall length is six amino acids.

4. The therapeutic peptide of claim 1 wherein said peptide overall length is seven amino acids.

5. The therapeutic peptide of claim 1 wherein said peptide overall length is eight amino acids.

6. The therapeutic peptide of claim 1 wherein said peptide overall length is nine amino acids.

* * * * *